US008828464B2

(12) United States Patent
Atkin et al.

(10) Patent No.: US 8,828,464 B2
(45) Date of Patent: Sep. 9, 2014

(54) WHITENED EXINE SHELLS (75) Inventors: Stephen Atkin, Hessle (GB); Stephen Beckett, Wiggington (GB); Grahame Mackenzie, Hull (GB)

(73) Assignee: University of Hull, Hull (GB)

( * ) Notice: Subject to any disclaimer, the term of this patent is extended or adjusted under 35 U.S.C. 154(b) by 440 days.

(21) Appl. No.: 13/001,767

(22) PCT Filed: Jul. 9, 2009

(86) PCT No.: PCT/GB2009/050813
§ 371 (c)(1),
(2), (4) Date: Jan. 26, 2011

(87) PCT Pub. No.: WO2010/004334
PCT Pub. Date: Jan. 14, 2010

(65) Prior Publication Data
US 2011/0117148 A1    May 19, 2011

(30) Foreign Application Priority Data
Jul. 9, 2008    (GB) .................................. 0812513.0

(51) Int. Cl.
| A61K 8/02 | (2006.01) |
| A61K 9/16 | (2006.01) |
| A61K 31/34 | (2006.01) |
| A23L 1/22 | (2006.01) |
| A23L 1/277 | (2006.01) |
| A23L 1/00 | (2006.01) |
| A01N 43/08 | (2006.01) |
| A61K 36/00 | (2006.01) |
| A61K 9/00 | (2006.01) |

(52) U.S. Cl.
CPC .. A61K 36/00 (2013.01); A61K 9/00 (2013.01)
USPC .............. 426/253; 426/89; 424/401; 424/490; 514/474

(58) Field of Classification Search
USPC .............. 424/401, 490; 426/253, 89; 514/474
See application file for complete search history.

(56) References Cited

U.S. PATENT DOCUMENTS

| 4,917,892 A | 4/1990 | Speaker et al. |
| 5,013,552 A | 5/1991 | Samir Amer et al. |
| 5,275,819 A | 1/1994 | Amer et al. |
| 5,368,840 A | 11/1994 | Unger |
| 5,508,021 A | 4/1996 | Grinstaff et al. |
| 5,648,101 A | 7/1997 | Tawashi |
| 6,156,330 A | 12/2000 | Tsukada et al. |
| 6,342,255 B1 | 1/2002 | De Gregorio |
| 7,182,965 B2 | 2/2007 | Maack |
| 7,608,270 B2 | 10/2009 | Beckett et al. |
| 7,758,888 B2 | 7/2010 | Lapidot et al. |
| 7,846,654 B2 | 12/2010 | Atkin et al. |
| 2003/0108596 A1 | 6/2003 | Sung |
| 2004/0197405 A1 | 10/2004 | Devane et al. |
| 2005/0002963 A1 | 1/2005 | Beckett et al. |
| 2005/0153862 A1 | 7/2005 | Lau et al. |
| 2005/0191374 A1 | 9/2005 | Maack |
| 2008/0112967 A1 | 5/2008 | Feng et al. |
| 2008/0188572 A1* | 8/2008 | Atkin et al. .................. 514/783 |
| 2008/0311213 A1 | 12/2008 | Atkin et al. |
| 2009/0246125 A1 | 10/2009 | Atkin et al. |
| 2011/0002984 A1 | 1/2011 | Atkin et al. |
| 2013/0309298 A1 | 11/2013 | Atkin et al. |

FOREIGN PATENT DOCUMENTS

| CN | 1 105 594 | 7/1995 |
| DE | 199 02 724 A1 | 7/2000 |
| DE | 102 16 772 A1 | 10/2003 |
| GB | 0427520.2 | 12/2004 |
| GB | 0515521.3 | 7/2005 |
| GB | 0516397.7 | 8/2005 |
| GB | 0724550.9 | 12/2007 |
| GB | 0812513.0 | 7/2008 |
| JP | 59-116208 | 7/1984 |
| JP | 03-501485 | 4/1991 |
| JP | 04-341157 | 11/1992 |
| JP | 11-506451 | 6/1999 |
| WO | WO96/38159 | 12/1996 |
| WO | WO99/49063 | 9/1999 |
| WO | WO01/80823 A2 | 11/2001 |
| WO | WO02/55561 A1 | 7/2002 |
| WO | WO03/078048 A2 | 9/2003 |
| WO | WO03/094942 A1 | 11/2003 |

(Continued)

OTHER PUBLICATIONS

US Office Action dated Feb. 6, 2007 issued in U.S. Appl. No. 10/877,042.
US Final Office Action dated Oct. 16, 2007 issued in U.S. Appl. No. 10/877,042.
US Office Action dated May 5, 2008 issued in U.S. Appl. No. 10/877,042.
US Office Action (Interview Summary) dated Oct. 16, 2008 issued in U.S. Appl. No. 10/877,042.
US Final Office Action dated Nov. 7, 2008 issued in U.S. Appl. No. 10/877,042.
US Office Action (Advisory Action) dated Dec. 22, 2008 issued in U.S. Appl. No. 10/877,042.
US Office Action (Interview Summary) dated Mar. 9, 2009 issued in U.S. Appl. No. 10/877,042.

(Continued)

*Primary Examiner* — Gina C Justice
*Assistant Examiner* — Genevieve S Alley
(74) *Attorney, Agent, or Firm* — Jennifer L. Wahlsten; Emily M. Haliday; Weaver Austin Villeneuve & Sampson LLP (57) ABSTRACT

A whitened exine shell having a degree of whiteness (L*) of greater than 65 measured under D 65 illumination. The shell can be used as a delivery vehicle for an active substance, or as an antioxidant. It can be used in a method of surgery, therapy or diagnosis. The invention provides a formulation containing the whitened exine shell together with an active substance; and a method for preparing the shell by isolating an exine shell from a naturally occurring spore under treatment conditions which do not include aceto lysis, and treating the isolated shell or a precursor thereof with a bleaching composition.

17 Claims, 3 Drawing Sheets

(56) References Cited

FOREIGN PATENT DOCUMENTS

| WO | WO2005/000280 A2 | 1/2005 |
|---|---|---|
| WO | WO 2006/064227 | 6/2006 |
| WO | WO 2006/108595 | 10/2006 |
| WO | WO 2007/012856 | 2/2007 |
| WO | WO 2007/012857 | 2/2007 |
| WO | WO 2009/077749 | 6/2009 |
| WO | WO 2010/004334 | 1/2010 |

OTHER PUBLICATIONS

US Notice of Allowance dated Jun. 22, 2009 issued in U.S. Appl. No. 10/877,042.
US Examiner Interview Summary dated Feb. 16, 2011 issued in U.S. Appl. No. 11/721,782.
US Office Action dated Mar. 17, 2011 issued in U.S. Appl. No. 11/721,782.
US Final Office Action dated Oct. 17, 2011 issued in U.S. Appl. No. 11/721,782.
US Office Action dated Dec. 10, 2009 issued in U.S. Appl. No. 12/020,444.
US Office Action Final dated Apr. 26, 2010 issued in U.S. Appl. No. 12/020,444.
US Notice of Allowance dated Aug. 2, 2010 issued in U.S. Appl. No. 12/020,444.
US Office Action (Restriction Requirement) dated Jul. 28, 2011 issued in U.S. Appl. No. 11/996,948.
US Office Action dated Dec. 1, 2011 issued in U.S. Appl. No. 11/996,948.
US Final Office Action dated Jun. 15, 2012 issued in U.S. Appl. No. 11/996,948.
US Office Action (Restriction Requirement) dated Feb. 9, 2012 issued in U.S. Appl. No. 12/747,484.
US Office Action dated May 4, 2012 issued in U.S. Appl. No. 12/747,484.
PCT International Search Report dated Apr. 25, 2005 issued in PCT/GB2004/002775.
PCT International Preliminary Report on Patentability and Written Opinion dated Jan. 3, 2006 issued in PCT/GB2004/002775.
UK Search Report dated Dec. 15, 2003 issued in GB 0315019.0.
PCT Written Opinion dated Mar. 24, 2006 issued in PCT/GB2005/004824 (WO 2006/064227).
PCT International Search Report dated Mar. 27, 2006 issued in PCT/GB2005/004824 (WO 2006/064227).
PCT International Preliminary Report on Patentability dated Jun. 19, 2007 issued in PCT/GB2005/004824 (WO 2006/064227).
PCT International Search Report dated Oct. 13, 2006 issued in PCT/GB2006/002800 (WO 2007/012856).
PCT International Preliminary Report on Patentability and Written Opinion dated Jan. 29, 2008 issued in PCT/GB2006/002800 (WO 2007/012856).
PCT International Search Report dated Oct. 13, 2006 issued in PCT/GB2006/002802 (WO 2007/012857).
PCT International Preliminary Report on Patentability and Written Opinion dated Jan. 29, 2008 issued in PCT/GB2006/002802 (WO 2007/012857).
UK Search Report and Examination Opinion dated Dec. 7, 2005 issued in GB 0516397.7.
PCT International Search Report and Written Opinion dated May 15, 2009 issued in PCT/GB2008/004150.
UK Search Report dated Apr. 21, 2008 issued in GB 0724550.9.
PCT International Search Report and Written Opinion dated Dec. 15, 2009 issued in PCT/GB2009/050813.
UK Search Report dated Nov. 26, 2008 issued in GB 0812513.0.
UK Search Report dated Oct. 26, 2009 issued in GB 0911927.2.
Adamson et al., (Nov. 1983) "New applications of sporopollenin as a solid phase support for peptide synthesis and the use of sonic agitation" *International Journal of Peptide and Protein Research*, 22(5):560-564.

Ahlers et al., (Mar.-Apr. 2000)"The Nature of Oxygen in Sporopollenim from the Pollen of *Typha angustifolia* L.", *Journal of Biosciences*, 55(3-4):129-136.
Bohne et al., (2003) "Diffusion Barriers of Tripartite Sporopollenin Microcapsules Prepared from Pine Pollen", *Annals of Botany* 92:289-297.
Clark, Andy (Sep./Oct. 2002) "Formulation of proteins and peptides for inhalation", *dds&s*, 2(3):73-77.
Crockford et al., (Dec. 2002/Jan. 2003) "Adaptive Aerosol Delivery (AAD™) technology: drug delivery technology that adapts to the patient", *dds&s*, 2(4):110-113.
Diego-Taboada et al., (Winter 2007) "Pollen: a Novel Encapsulation Vehicle for Drug Delivery", *Innovations in Pharmaceutical Technology*,200712 GB, NR 24, XP009126863, pp. 63-66.
Gregoriadis, Gregory (Dec. 2002/Jan. 2003) "Liposomes in drug and vaccine delivery", *dds&s*, 2(4):91-97.
Hamilton et al., (1984) "Survey for Prunus Necrotic Ringspot and Other Viruses Contaminating the Exine of Pollen Collected by Bees", *Canadian Journal of Plant Pathology*, 6(3):196-199, Abstract Only, 1 page.
Ivleva et al., (2005) "Characterization and discrimination of Pollen by Raman microscopy", *Analytical and Bioanalytical Chemistry*, 381(1):261-267.
Erdtman, G., (1960) "The Acetolysis Method, a Revised Description", *Svensk Botanisk Tidskrift*, 54(4): 561-564.
Jordan et al. (Mar. 31, 2006) "Activity of bleach, ethanol and two commercial disinfectants against spores of *Encephalitozoon cuniculi*", Veterinary Parasitology, Elsevier Science, Amsterdam, NL, XP025025599,136(3-4):343-346.
Jorde et al., (1974) "ZUR Persorption Von Pollen UND Sporen Durch Die Intake Darmschleimhuat", *Acta Allergologica*, 29:165-175.
Kennedy et al., (Feb. 17, 2004) "Synthesis and characterization of tubular amphiphilic networks with controlled pore dimensions for insulin delivery", Abstract Only, Retrieved on Feb. 17, 2004 from http://wost.wok.mimas.ac.uk:8000/C1W.cgi., 1 page.
Nitz, Otto W., "Essential Oil" (2011) *Encyclopedia Americana*, Grolier Online http://ea.grolier.com/article?id=0146680-00, downloaded on Oct. 27, 2011, 2 pages.
Odén et al. (1992) Demonstration of superoxide dismutase enzymes in extracts of pollen and anther of *Zea mays* and in two related products, Baxtin® and Polbax®, *Grana*, 31:76-80.
Paunov et al. (2007) "Sporopollenin micro-reactors for in-situ preparation, encapsulation and targeted delivery of active components" *Journal of Materials Chemistry*, 17:609-612.
Penny, J. (Dec. 2002/Jan. 2003) "Bioavailability of orally delivered therapeutics: a biological perspective", *dds&s*, 2(4):100-102.
Polysciences, Inc., (Oct. 1999) "*Sporopollenin Microparticles*", Technical Data Sheet 281:1-2.
Reslow et al., (Dec. 2002/Jan. 2003)"Sustained-release of human growth hormone from PLG-coated starch microspheres", *dds&s*, 2(4):103-109.
Shaw, G. Sykes, M., Humble R.W., MacKenzie, G., Marsdan, D. & Pehlivan, F. (Nov. 1, 1988) "The Use of Modified Sporopollenin from *Lycopodium clavatum* as a Novel Ion-or Ligand-Exchange Medium", *Reactive Polymers* 9(2):211-217.
Smith, Ian (Dec. 2002/Jan. 2003) "Bioavailability, targeting and controlled release—the key to effective drug delivery?", *dds&s*, 2(4):89.
Soler et al., (1977) "Technical procedure for tagged pollen aerosols for the study of their penetration in the bronchial tree", *Clinical Respiratory Physiology*, France, 13(4):499-511, abstract only.
"Sporomex Ltd: oral and respirable drug delivery", Page last modified on Mar. 2, 2005, www.sporomex.co.uk, 5 pages.
Stagg, Charles M., Feather, Milton S. (1973) "The Characterization of a Chitin-Associated$_D$-Glucan from the Cell Walls of *Aspergillus niger*", *Biochim Biophys Acta*, 320:64-72.
Stanley, R.G., Linskens, H.F. (1974) Pollen: Biology, Biochemistry Management, New York, Springer-Verlag, 114-115, 179-181.
Twell, David (2001) "Pollen: Structure, Development and Function", *Encyclopedia of Life Sciences, MacMillan Publishers, London, GB*, XP-002526079, [Retrieved from the Internet: URL:http://mrw.interscience.wiley.com/emrw/9780470015902/els/article/a0002039/current/pdf], 6 pages.

(56) References Cited

OTHER PUBLICATIONS

Weiner, M.L., (1998) "Intestinal Transport of Some Macromolecules in Food", *Fd Chem. Toxic*, 26(10):867-880.

Wiseman, Alan (Dec. 2002/Jan. 2003) "Targeted membrane-penetrating peptides: identify candidate drug-cargoes in silico?", *dds&s*, 2(4):114.

Wiseman, Alan (Dec. 2002/Jan. 2003) "Cell-Penetrating Peptides. Processes and Applications", *dds&s*, 2(4):115.

Wittborn et al., (1998) "Nanoscale Similarities in the Substructure of the Exines of *Fagus* Pollen Grains and *Lycopodium* Spores", *Annals of Botany* 82:141-145.

US Office Action dated Jun. 14, 2013 issued in U.S. Appl. No. 11/996,948.

US Notice of Allowance dated Mar. 14, 2014 issued in U.S. Appl. No. 11/996,948.

US Final Office Action dated Feb. 28, 2013 issued in U.S. Appl. No. 12/747,484.

US Office Action dated Jan. 31, 2014 issued in U.S. Appl. No. 13/928,129.

Barrier et al., (2010) "Viability of Plant Spore Exine Capsules for Microencapsulation," *Journal of Materials Chemistry*, This journal is © The Royal Society of Chemistry 2010, [Downloaded by University of Hull on Nov. 12, 2010], Published on Nov. 12, 2010 on http://pubs.rsc.org/doi:10.1039/C0JM02246B, 7 pp.

Binks et al., (2005) "Naturally Occurring Spore Particles at Planar Fluid Interfaces and in Emulsions," *Langmuir*, 21(18):8161-8167.

Brooks, (Aug. 3, 1968) "Chemical Structure of the Exine of Pollen Walls and a New Function for Carotenoids in Nature," *Nature*, 219:532-533.

Brooks et al., (1968) "The Post-Tetrad Ontogeny of the Pollen Wall and the Chemical Structure of the Sporopollenin of Lilium Henryi," *Grana Palynologica*, 8(2-3):227-234 [Downloaded by University of Hull on Feb. 12, 2014].

Diego-Taboada et al., (2012) "Sequestration of Edible Oil from Emulsions Using New Single and Double Layered Microcapsules from Plant Spores," *Journal of Materials Chemistry*, 22:9767-9773.

Dominguez et al., (1999) "Pollen sporopollinin: degradation and structural elucidation," *Sex Plant Reprod*, 12:171-178.

Hemsley et al., (2004) "The Evolution of Plant Physiology," *Elsevier Academic Press*, p. 139.

Herminghaus et al., (1988) "The Occurrence of Phenols as Degradation Products of Natural Sporopollenin—a Comparison with "Synthetic Sporopollenin"," *Supplied by the British Library—"The world's knowledge,"* pp. 491-500.

Kawase et al., (1996) "Gas Chromatography-Mass Spectrometric Analysis of Oxidative Degradation Products of Sporopollenin in *Magnolia grandiflora* (Magnoliaceae) and *Hibiscus syriacus* (Malvaceae)," *J. Plant Research, The Botanical Society of Japan*, 109:297-299, p. 297.

Shaw et al., (Jan. 1, 1966) "Chemical Studies on the Constitution of Some Pollen and Spore Membranes," *J. Chem. Soc. (C)*, pp. 16-22 [Downloaded on Dec. 2, 2014 by University of Hull].

Shaw et al., (1971) "Chemistry of Sporopollenin," *Proceedings of a Symposium held at the Geology Department, Imperial College*, London Sep. 23-25, 1970, pp. 312-319.

Shaw et al., (1964) "Chemical Studies on the Constitution of Some Pollen and Spore Membranes," *Grana palynologica*, 5(2):247-252 [Downloaded by University of Hull on Feb. 12, 2014].

Traverse, Alfred, (2007) Paleopalynology: Second Edition, *Topics in Geobiology*, Springer, vol. 28, p. 60.

\* cited by examiner

WHITENED EXINE SHELLS

FIELD OF THE INVENTION

This invention relates to exine shells which are usable as delivery vehicles for active substances and as antioxidants.

BACKGROUND TO THE INVENTION

It is known from WO-2005/000280 to use the exine coatings of naturally derived (typically plant) spores as delivery vehicles for active substances such as pharmaceuticals and dietetic substances. These coatings can be isolated from spores by successive treatments, for example with organic solvents, alkali and acid so as to remove the lipid, carbohydrate, protein and nucleic acid components that may be attached to or contained within the exine shell. Enzymatic methods have also been used to isolate the exine coating from other components of a spore.

Exine coatings (or shells) take the form of essentially hollow capsules that can be impregnated or filled with, or chemically or physically bound to, another substance. According to WO-2005/000280, a pharmaceutical or dietetic active substance may be physically or chemically bound to, adsorbed on or more typically encapsulated within such a hollow exine shell. The exine/active substance combination may then be formulated—often mixed with conventional excipients, diluents or carriers and/or with release rate modifiers—for the desired mode of delivery, for example oral, buccal or pulmonary delivery.

WO-2007/012857 discloses the use of exine shells as delivery vehicles in topical formulations. This document describes how the exine shells, despite their mechanical and chemical strength, can be caused, by gentle rubbing, to release a substance encapsulated within them. This makes the exine shells particularly suitable for topical delivery of substances, such as cosmetics or sunscreens, to surfaces such as the skin.

Sometimes, when formulating an active substance, it is necessary to protect the substance, at least temporarily, from external influences such as light, moisture or oxygen (air). This may be for the purpose of improving the storage stability of the formulation, or it may be to ensure that the formulation reaches, following its delivery to a patient, the appropriate part of the body.

Exine shells can themselves provide a degree of protection for an encapsulated active substance, for instance from atmospheric effects such as light and/or oxygen (air), and therefore from premature degradation. The physical protection they provide can also help reduce loss of the active substance by evaporation, diffusion or leaching. It has also been found (as disclosed in WO-2007/012856) that in many cases an exine shell can itself act as an antioxidant, rather than merely as a physical barrier to oxygen (air), this effect being observable even when an active substance is outside of, rather than encapsulated within, the shell.

Useful exine coatings may be isolated from spores by successive treatments with organic solvents, alkali and acid so as to remove the lipid, carbohydrate, protein and nucleic acid components that may be attached to or contained within the exine shell. In WO-2007/012856 such exine shells isolated by acid hydrolysis (for example, with phosphoric acid) followed by base hydrolysis (for example, with potassium hydroxide) are designated "AHS". Also disclosed are exine shells designated "BHS" which were subjected only to base hydrolysis (for example, with potassium hydroxide). The BHS samples comprised not only the exine shell but also a proportion of the cellulosic intine layer normally removed during the acid treatment. It was found that some BHS exine coatings were particularly effective in reducing the oxidation rates of oils encapsulated therein when exposed to UV light.

Exine coatings produced by methods disclosed in the foregoing documents are typically chocolate brown in colour. Such a coloured product can be undesirable for many applications. For example, in the case of cosmetics, food products and certain pharmaceutical applications, dark particles may be visible within a lighter product or may appear to discolour it. Even if it is desired to colour the product, a dark exine delivery vehicle may still be visible or may reduce the attractiveness of the applied colour, for example by making it appear dull or muddy. There can be a need, therefore, to lighten the colour of exine coatings used as delivery vehicles in such applications, and a creamy or relatively pale colour can be highly desirable.

In *Svensk Botanisk Tidskrift*, 54, 4 1960 by G Erdtman, there is described a method for preparing herbarium material for mounting on optical microscope slides. Powdered flowers, buds or isolated stamens were subjected to acetolysis using a mixture of acetic anhydride and concentrated sulphuric acid at 70° C. This relatively harsh acetolysis procedure for isolating pollen grains in preparation for mounting on microscope slides caused the grains to become so much darker in colour, especially in spores from species such as *Geranium* and *Scabiosa*, that they could not be microscopically observed. Therefore, before such observations were carried out, the pollen grains had to be bleached. Bleaching was undertaken using glacial acetic acid, saturated sodium chlorate solution and concentrated hydrochloric acid. However, as shown in Comparative Example 14 below, the end product of this process still has a degree of whiteness insufficient to be suitable for use in food, cosmetics and pharmaceuticals. In addition, the use of Erdtman's method tends to cause fragmentation of the pollen shells, which was acceptable in the context of preparing a sample for microscopic study.

Such fragmentation is not surprising, since sporopollenin is known to be degraded by exposure to oxidising agents (see G. Shaw, "*The chemistry of sporopollenin*." in J. Brooks et al. (eds.) *Sporopollenin*. (1971) London & New York: Academic Press, p. 305-348). Therefore, there is a disincentive to subject exine shells to bleaching in order to lighten their colour, where the shells are intended for use as delivery vehicles (e.g., WO-2005/000280 & WO-2007/012857), for which purpose substantially intact shells are required. As well as being expected to compromise the structural integrity of the resultant shells, bleaching might also be expected to compromise their antioxidant properties such as were described in WO-2007/012856. Oxidative degradation and loss of antioxidant effects could both be detrimental for shells intended to be used as delivery vehicles in for example foods, cosmetics and pharmaceuticals.

Surprisingly, however, the present inventors have found that exine shells prepared under hydrolysis treatment conditions can be whitened to an appropriate degree without undue structural degradation, despite the vulnerability of sporopollenin to oxidative degradation. Such shells have also been found to retain antioxidant activity. The resultant whitened exine shells can be suitable for encapsulating active substances for delivery, especially in foods, cosmetics and pharmaceuticals.

STATEMENTS OF THE INVENTION

According to a first aspect of the present invention there is provided a whitened exine shell having a degree of whiteness (L*) as defined herein of greater than about 65 measured under D 65 illumination. The exine shell may be usable as a delivery vehicle for an active substance. It may be usable as an antioxidant.

In embodiments of the invention, the exine shell has a degree of whiteness (L*) as defined herein of greater than about 70 measured under D 65 illumination, or of greater than about 74 or 75 or 76 or 77 or 78 or 79 or 80 or 85 or 90.

Such shells typically have an Infra Red spectroscopy band between 1110 $cm^{-1}$ and 1180 $cm^{-1}$ of lower intensity compared to that of an exine shell having a degree of whiteness of less than 65 measured under D 65 illumination. Also, after bleaching, the band between 1110 $cm^{-1}$ and 1180 $cm^{-1}$ is typically diminished in intensity as the band between 1650 $cm^{-1}$ and 1750 $cm^{-1}$ is typically increased, compared with unbleached shells. Hypothetically (and without being bound by theory), this pattern may be the result of oxidation of primary or secondary alcohol groups (detected between 1110 $cm^{-1}$ and 1180 $cm^{-1}$) on the exine surface to carbonyl groups (detected between 1650 $cm^{-1}$ and 1750 $cm^{-1}$); this change may contribute to the observed change in whiteness.

The shell may be a whitened AHS exine shell, or a whitened BHS exine shell, or a whitened enzyme extracted exine shell, as defined below. It is suitably active as an antioxidant.

In an embodiment of the invention, the whitened exine shell may be intact or substantially so. In other words, apart from the micro- or nanopores which are naturally present in the surfaces of such shells, it will provide a continuous outer wall defining an inner cavity into which an active substance can be loaded. The exine shell may however be broken or damaged in parts; the invention thus embraces a fragment of a whitened exine shell. Suitably, however, the exine shell is continuous over at least about 50%, suitably at least about 75 or 80 or 85 or 90%, of the surface area which an exine shell from the relevant species would have if intact.

A second aspect of the invention provides a formulation containing an active substance and a whitened exine shell according to the first aspect. The formulation may in particular be a food product, a cosmetic product, or a pharmaceutical or dietetic (which includes nutraceutical) product.

According to a third aspect, the invention provides a method for preparing a whitened exine shell, such as an exine shell according to the first aspect, the method involving isolating an exine shell from a naturally occurring spore under hydrolysis treatment conditions and treating the isolated exine shell or a precursor thereof with a bleaching composition. The isolated exine shell may be an AHS or a BHS exine shell or an enzyme extracted exine shell as defined herein, or a shell isolated by a combination of extraction methods.

A precursor of an isolated exine shell may be a naturally occurring ("raw") spore, or a raw spore from which components other than the exine shell (for example lipids, proteins and nucleic acids) have been only partially extracted. Thus, the bleaching composition may be applied before, during or after the exine shell isolation step. In an embodiment, it is applied to the isolated exine shell.

In an embodiment of the third aspect the exine shell or exine shell precursor is treated with the bleaching composition for a length of time and at a temperature such as to achieve a degree of whiteness (L*) in the resultant product of greater than about 65 measured under D 65 illumination, or of greater than about 70 or 74 or 75 or 76 or 77 or 78 or 79 or 80 or 85 or 90.

According to a fourth aspect of the invention there is provided the use of a whitened exine shell according to the first aspect as an antioxidant. A fifth aspect provides the use of such a whitened exine shell as a delivery vehicle for an active substance. The active substance may be chemically or physically bound to, or encapsulated within, the exine shell. In an embodiment, it is encapsulated within the exine shell.

A sixth aspect of the invention provides a whitened exine shell according to the first aspect, for use in a method of surgery, therapy or diagnosis practised on a living human or animal body. The exine shell may thus be used as a delivery vehicle for a substance which is active as a pharmaceutical or diagnostic agent. A seventh aspect of the invention provides the use of a whitened exine shell according to the first aspect, in the manufacture of a medicament for the delivery of a pharmaceutically active substance or a diagnostic agent to a human or animal patient.

According to an eighth aspect of the present invention there is provided a method for protecting an active substance from oxidation and/or for increasing the stability of the active substance or of a composition containing it, the method comprising formulating the active substance with a whitened exine shell according to the first aspect of the invention.

A ninth aspect provides a method of improving the whiteness of an exine shell which has been isolated from a naturally occurring spore under hydrolysis conditions, the method involving treating the isolated exine shell or a precursor thereof with a bleaching composition.

As used herein, the term "degree of whiteness (L*)" means the whiteness value of a tableted sample measured using a Gretag Macbeath™ 7000A Colour-eye instrument or equivalent used in the reflectance mode. This instrument provides a choice of light sources: "D65" represents roughly a mid-day sun in western and northern Europe, whilst "illuminant A" is intended to represent typical, domestic, tungsten-filament lighting and "CWF 2" represents cool white fluorescent. The instrument thus provides a standard measure of whiteness (L*) that can be determined for daylight, tungsten and fluorescent lighting conditions. Under each set of lighting conditions L* is defined such that 100 is fully white and 0 has no white components.

For the purposes of this invention, the "D65" illuminant is used to measure whiteness. Further details of standard sample preparation and the measurement of L* are provided in the examples below. Repeatability trials in which the whiteness of a given sample was measured on several different occasions showed reproducible results. Similarly, the measurement of relative whiteness (L*) of a number of different samples correlated well with the visual perception of relative whiteness by a panel of volunteers.

Conventionally, exine shells are produced from naturally derived (typically plant) spores and can be isolated from such spores by successive treatments with organic solvents, alkali and acid so as to remove the lipid, carbohydrate, protein and nucleic acid components that may be attached to or contained within the shell. Alternatively, either the base or the acid treatment stage may be omitted to provide an exine shell in which at least a proportion of the cellulosic intine shell is retained. Shells can also be prepared by enzyme-catalysed extraction.

The present inventors have found that, surprisingly, the desired level of whiteness is best achieved using a combination of (i) a hydrolysis extraction method to isolate the exine shell and (ii) suitable bleaching compositions. Many previously used isolation methods darkened the exine shell product to such an extent that it could not then be whitened to an acceptable degree. Unexpectedly, exine shells isolated using the non-acetolysing hydrolysis methods disclosed herein can withstand bleaching—in particular oxidative bleaching—to achieve the stated level of whiteness without structural degradation, despite the known vulnerability of sporopollenin to degradation by oxidising agents.

An exine shell is the outer coating from around a naturally occurring ("raw") spore. It may consist in part or mainly of sporopollenin. It may be of a type described in WO-2005/000280, in particular at pages 4, 8 and 9 and in Example 1.

According to the present invention, the exine shell may be derived from any suitable naturally occurring spore, whether microbial, plant or animal in origin. In this context, the term "plant" is to be construed in its broadest sense, and embraces for example mosses, fungi, algae, gymnosperms, angiosperms and pteridosperms. Moreover the term "spore" is used to encompass not only true spores such as are produced by ferns, mosses and fungi, but also pollen grains, as are produced by seed-bearing plants (spermatophytes) and also endospores of organisms such as bacteria. Similarly, the term "naturally occurring" means that a spore is produced by a living organism, whether prokaryote or eukaryote and whether plant or animal. The spore (which term includes pollen grains and also endospores of organisms such as bacteria) may for instance be derived from a plant, or from a fungus, alga or bacterium or other micro-organism.

Suitable organisms from which such spores may be obtained include the following, the approximate diameters of their spores, as published in the literature (e.g., Moore et al. "Pollen analysis" $2^{nd}$ ed. (1991) Oxford: Blackwell Science Publication), being shown in the second column. Where measurements in the literature are unavailable or inconsistent, the values determined by the inventors are marked with an asterisk.

|  |  |
|---|---|
| *Bacillus subtilis* | 1.2 μm |
| *Myosotis* ("forget-me-not") | 2.4-5 μm |
| *Aspergillus niger* | 4 μm |
| *Penicillium* | 3-5 μm |
| *Cantharellus minor* | 4-6 μm |
| *Ganomerma* | 5-6.5 μm |
| *Agrocybe* | 10-14 μm |
| *Urtica dioica* | 10-12 μm |
| *Periconia* | 16-18 μm |
| *Epicoccum* | 20 μm |
| Ryegrass "*Lolium perenne*" | 21 μm |
| Timothy grass | 22 μm |
| Cereal rye "*Secale cereale*" | 42 μm |
| *Lycopodium clavatum* | 26 μm* |
| "*Lycopodium* powder" | 40 μm |
| Maize "*Zea mays*" | 80 μm* |
| Hemp "*Cannabis sativa*" | 24 μm* |
| Rape hemp | 25 μm* |
| Wheat | 23 μm |
| *Abies* | 125 μm |
| *Cucurbitapapo* | 200 μm |
| *Cuburbita* | 250 μm |

Of these, *Lycopodium clavatum*, *lycopodium* powder, ryegrass, cereal rye, Timothy grass, hemp, rape, wheat and maize pollen spores may be preferred. Other spores from which exine shells may be extracted are disclosed in the publications referred to at page 8 of WO-2005/000280.

The exine shell may have a diameter (which may be determined by scanning electron microscopy) of about 1 μm or greater, or of about 3 or 5 or 8 or 10 or 12 or about 15 μm or greater. It may have a diameter of up to about 300 μm, or of up to about 250 or 200 or 150 or 100 or 80 or 50 or 40 μm. For example, its diameter may be from 1 to 300 μm, or from 1 to 250 μm, or from 3 to 80 μm, or from 3 to 50 μm, or from 15 to 40 μm. Grass pollen-derived exines, as well as other exine shells of approximately 20 μm diameter, might also be expected to be suitable, as may pollen exines having diameters of up to around 80 μm. For delivery into the bloodstream, exine shells having diameters of less than about 40 μm, for example of about 35 μm or about 32 μm or even about 30 μm or less, may be most suitable.

Exine shells and exine shell precursors for use in the present invention generally have an initially chocolate brown colour (whiteness under D 65 illumination of about 50 to 65). The initial colour of the exine shell or precursor may vary depending on the particular spore used and the conditions under which it was isolated.

In the context of the present invention, "hydrolysis" treatment conditions for the isolation of exine shells from spores means conditions which are suitable for extracting the lipid, protein, nucleic acid and, if applicable, the carbohydrate components of the spores, but which do not involve acetolysis. This may be carried out by, for example, heating in the presence of either aqueous acid at a temperature of at least 60° C. or aqueous base at a temperature of at least 70° C. (in either case, at atmospheric pressure when at sea level). Acid or base treatments can be used in isolation or sequentially. Examples of suitable treatment conditions are described herein, in particular in the examples below, and also in WO-2007/012856 and WO-2007/012857. Enzyme-catalysed hydrolysis may also be employed.

According to the invention, exine shells may be isolated from naturally occurring (raw) spores by hydrolysis, for example, using acid and/or base hydrolysis and/or enzyme-catalysed hydrolysis. The acid may be inorganic, mineral or organic and is preferably not sulphuric acid or nitric acid. The base may be inorganic, mineral or organic. Hydrolysis may be enzyme-catalysed and the enzyme may be, for example, a cellulase.

Acidic conditions alone may be employed provided that acetolysis conditions are avoided. It may, for example, be preferred not to use concentrated sulphuric acid in the presence of acetic anhydride. Extraction using an aqueous mineral acid such as, for example, concentrated hydrochloric acid or ortho-phosphoric acid may prove acceptable in the absence of an extraction stage under basic conditions.

In general, raw exine shells will firstly be defatted by treatment with a suitable solvent. A typical treatment is to suspend raw spores in acetone and stir under reflux, or at a temperature of from about 50° C. to reflux, for an effective time, usually about four hours. The resultant defatted shells can then be filtered and dried.

The defatted exine shells can then be treated under basic conditions to remove proteinaceous material. A typical treatment involves suspension in an aqueous alkali metal base (for example potassium hydroxide) for sufficient time to reduce residual protein content to below 10% w/w protein, for example, 5% w/w protein, for example, 1% w/w protein, for example, 0.5% w/w protein, for example, below 0.1% w/w protein. In general, suspension of defatted shells in 6% w/v aqueous potassium hydroxide and stirring under reflux or from about 70° C. to reflux for about 6 to 12 hours is sufficient to achieve the desired reduction in protein levels. Suitably, the treatment with base takes place in two or more separate stages, with washing in between. For example, two separate treatments with potassium hydroxide for about 6 hours each with washing in between has been found to be particularly effective.

The resultant exine shells, which have been subjected to base extraction but which have not been subjected to extraction under acidic conditions, are referred to herein as "base hydrolysed" or "BHS" exine shells. Extraction under alkaline conditions fails to remove, or only partially removes, the cellulosic intine layer. Thus a BHS exine shell is generally characterised by at least partial retention of the cellulosic intine layer.

In one embodiment of the invention a BHS exine shell is treated with a bleaching composition. It will be appreciated that if an acidic bleaching agent is used, the bleaching treatment may itself remove a proportion of the intine layer.

Optionally, an unbleached BHS exine shell may be further subjected to extraction under acidic conditions to remove the intine layer. Exine shells which have been isolated by extraction under both basic and acidic conditions are referred to herein as "acid hydrolysed" or "AHS" exine shells. Acids suitable for the preparation of AHS shells include phosphoric acid and concentrated hydrochloric acid. It is generally preferred not to use concentrated sulphuric acid or nitric acid for the acid extraction stage. Acidic extraction may take place, for example, in the presence of an acid such as ortho-phosphoric acid. In general, treatment with, for example, 85% v/v ortho-phosphoric acid for about 7 days under reflux, or from 50° C. to reflux, will be sufficient to effect substantial removal of the intine layer. The inventors have found that treatment with 85% w/v ortho-phosphoric acid at a temperature of about 60° C. for about 5 days combines sufficient removal of the intine layer with excellent preparation of the exine shell for bleaching.

An AHS exine shell in which the intine layer has been substantially completely removed is referred to herein as a "fully hydrolysed" AHS exine shell. It will be appreciated, however, that only partial removal of the intine layer may take place if the acidic extraction does not go to completion. Thus, in terms of the retention of the intine layer, there is a continuum between the BHS exine shell (which has not been subjected to acid hydrolysis) and a fully hydrolysed AHS exine shell. As used herein, the term "AHS exine shell" includes both a partially hydrolysed AHS shell containing some residual intine layer and a fully hydrolysed AHS shell containing substantially no intine layer.

An exine shell which has been extracted using enzyme-catalysed hydrolysis is known as an "enzyme extracted exine shell" and may have none, some or all of the naturally occurring intine layer remaining. An enzyme extracted exine shell in which the intine layer has been substantially completely removed is referred to as a "fully hydrolysed" enzyme extracted exine shell. Enzyme catalysed hydrolysis may be carried out at from 30° C. to 90° C. for 20 to 90 minutes, for example at from 35° C. to 50°, for example at about 40° C. for about an hour.

Any combination of base, acid and/or enzyme-catalysed hydrolysis may be employed to extract an exine shell.

In applications for which proteins represent potentially allergenic components of the original spore, it may be preferred that the extracted exine shells contain less than 10% protein by weight. They may have a protein level by weight of about 5% or less, or of about 2 or 1 or 0.5 or 0.2 or about 0.1% or less.

Following treatment with a bleaching composition and optional washing, the bleached exine shells may be used as delivery vehicles or as antioxidants without further treatment. If desired, however, bleached BHS exine shells may be further extracted under acidic conditions, or using enzyme-catalysed hydrolysis, to remove any residual intine layer. Bleached enzyme extracted exine shells may be further extracted under acid and/or basic conditions, to remove any residual intine layer.

In the method of the invention the bleaching composition may be applied:
(i) prior to or in the course of the extraction process used to isolate the exine shells; or
(ii) following enzyme-catalysed hydrolysis extraction, with or without additional acid and/or base extraction; or
(iii) following base extraction but without acid extraction; or
(iv) following both base and acid extraction; or
(v) following acid extraction under conditions excluding acetolysis and without base extraction.

The bleaching composition may be applied to an exine shell precursor, that is to say spores (typically plant spores) from which an exine shell can be isolated. It may be applied prior to the isolation step or during any desired stage of the isolation step. In an embodiment, however, the exine shell is treated with the bleaching composition after it has been at least partially isolated from spores.

In one embodiment the bleaching composition used in the present invention is an aqueous bleaching composition. It may be an oxidative bleaching composition. Suitable bleaching compositions include an aqueous hypochlorite solution, an aqueous chlorate solution, hydrogen peroxide, a perborate such as sodium perborate, a percarbonate such as sodium percarbonate, a hypochlorite such as calcium hypochlorite, an acyl peroxide such as benzoyl peroxide, peracetic acid, ozone, acetic acid in combination with sodium bisulphate, a hypochlorite optionally in combination with calcium peroxide, magnesium peroxide, nitrogen dioxide, chlorine, chlorine dioxide, azodicarbonamide, a sulphite such as sodium sulphite, a metabisulphite such as sodium metabisulphite, a percarbonate such as sodium percarbonate and tetraacetyle-neethylenediamine.

In an embodiment the bleaching composition is an aqueous hypochlorite, in particular aqueous sodium hypochlorite. There is suitably used from 3% by weight aqueous hypochlorite solution to a saturated hypochlorite solution, for example from 3% by weight to 15% by weight and more particularly about 7% by weight.

In an embodiment, the exine shell or exine shell precursor is treated with a bleaching composition for a length of time and at a temperature such that its degree of whiteness (L*) reaches at least 65. In general, the desired degree of whitening may be achieved following treatment with hypochlorite solution at a temperature of from room temperature to reflux, for example from about 50° C. to reflux, for example from room temperature to about 100° C. or from about 50° C. to about 100° C., for a time of from about 15 minutes to about 3 hours. If a relatively high temperature is used, for example from about 80° C. to about 100° C., a relatively shorter treatment time may be required, for example from about 15 minutes to about 1 hour. Good results have been obtained using a relatively lower temperature, for example from about room temperature to about 70° C., or from about 50° C. to about 70° C., for a longer time such as 1 to 3 hours. For example, the treatment may be carried out at about 80° C. for about 25 minutes, or at about 60° C. for about 2 hours. The sodium hypochlorite solution may typically be about 7% (w/v).

Alternatively, the bleaching composition may be an acidic aqueous solution of a chlorate, for example, a solution of sodium chlorate in hydrochloric acid or acetic acid or in a mixture of hydrochloric acid and acetic acid. Typically, there is used a saturated aqueous sodium chlorate solution in the presence of a concentrated acid such as hydrochloric acid or acetic acid or a mixture of concentrated acids, for example a mixture of concentrated hydrochloric acid and glacial acetic acid. The chlorate bleaching treatment suitably takes place at an elevated temperature, for example from about 50° C. to reflux or from about 70° C. to about 100° C. The chlorate bleaching treatment suitably continues for from about 30 minutes to about 2 hours. For example, the treatment may be carried out at about 95° C. for about an hour. One skilled in the art would readily be able to determine the appropriate conditions for use with other bleaching compositions.

Following treatment with the bleaching composition, the whitened exine shells may be used without further treatment but are preferably washed and then dried.

The whitened exine shells of the present invention may be formulated with conventional additives appropriate for the application envisaged. In particular, there may advantageously be employed brightening agents such as optical brightening agents, fluorescent brightening agents and fluorescent whitening agents typically used to enhance the appearance of fabric and paper. Such agents are intended to cause a "whitening" effect by making materials look less yellow and increasing the amount of light reflected to the eye. Suitable brightening agents will be well known to those skilled in the art. Examples include stilbenes and fluorescent dyes such as umbelliferone which adsorb energy in the UV portion of the spectrum and re-emit it in the blue portion of the visible spectrum. More specifically there may be employed triazine-stilbenes (di-, tetra- or hexa-sulphonated), biphenyl-stilbenes, biphenylcoumarins, imidazolines, diazoles, triazoles and benzoxazolines.

Since many brightening agents adsorb and re-emit light in particular portions of the spectrum, the presence of a brightening agent may interfere with the standard measurement of whiteness using a Gretag Macbeath 7000 A Colour-eye instrument as described herein. Suitably, therefore, the degree of whiteness is measured prior to the addition of any brightening agent, if used.

The scope of the present invention is not limited by any particular usage of the whitened exine shells. Examples of suitable uses are disclosed in WO-2005/000280, WO-2007/012856, WO-2007/012857 and PCT Application No. PCT/GB2008/004150, the contents of which are incorporated herein by reference.

In particular the shells may be used as delivery vehicles. There are inherent advantages to the use of naturally occurring exine shells as delivery vehicles, as described in WO-2005/000280 (for example at pages 3 and 4 and in the paragraph spanning pages 5 and 6) and WO-2007/012857 (see pages 4 to 5). Because of its inherent non-toxicity, for instance, a spore-derived exine shell can be particularly suitable for use as a delivery vehicle in the context of formulations which are likely to come into contact with, or be ingested by, the human or animal body. The proteinaceous materials which can otherwise cause allergic reactions to pollens are preferably removed or denatured during the processes used to isolate the exine component.

Naturally occurring exine shells have been found to be readily absorbed into, and broken down in, the bloodstream, as described in WO-2005/000280, making them ideal candidates for the systemic delivery of active substances such as pharmaceuticals or nutraceuticals. They can also be of value for the topical delivery of active substances, since they have been found capable of releasing an encapsulated active on application of only moderate pressure, for example gentle rubbing, as described in WO-2007/012857, in particular at page 3.

The exine shells prepared from any given organism also tend to be very uniform in size, shape and surface properties, unlike typical synthetic encapsulating entities. There is, however, significant variation in spore size and shape, and in the nature of the pores in the exine shells, between different species, allowing a formulation according to the invention to be tailored dependent on the nature and desired concentration of the active substance, the site and manner of intended application, the desired active substance release rate, the likely storage conditions prior to use and the like.

It can also be possible to encapsulate relatively high quantities of an active substance within even a small exine shell. The combination of high active loadings, small encapsulant size and adequate protective encapsulation is something which can be difficult to achieve using other known encapsulation techniques, and yet can be extremely useful in the context of preparing for example pharmaceutical or dietetic preparations, foods or beverages.

As described above, an exine shell is generally inert and non-toxic. Sporopollenin, for example, which is a component of many exine shells, is one of the most resistant naturally occurring organic materials known to man and can survive very harsh conditions of pressure, temperature and pH as well as being insoluble in most organic solvents (see G. Shaw, "The Chemistry of Sporopollenin" in *Sporopollenin*, J. Brooks, M. Muir, P. Van Gijzel and G. Shaw (Eds), Academic Press, London and New York, 1971, 305-348).

The ready, and often inexpensive, availability of spore exines, together with their natural origin, also make them highly suitable for use as active substance delivery vehicles.

The whitened exine shell of the present invention may be particularly suitable as a delivery vehicle for a cosmetic substance, for which colour is often of considerable importance. A cosmetic substance may for example be selected from makeup products (for example foundations, powders, blushers, eye shadows, eye and lip liners, lipsticks, other skin colourings and skin paints), skin care products (for example cleansers, moisturisers, emollients, skin tonics and fresheners, exfoliating agents and rough skin removers), fragrances, perfume products, essential oils, sunscreens and other UV protective agents, self tanning agents, after-sun agents, anti-ageing agents and anti-wrinkle agents, skin lightening agents, topical insect repellants, hair removing agents, hair restoring agents and nail care products such as nail polishes or polish removers. A perfume product may comprise more than one fragrance.

The whitened exine shell of the invention may be used as a delivery vehicle in a toiletry product which may be selected from soaps; detergents and other surfactants; deodorants and anti-perspirants; lubricants; fragrances; perfume products; dusting powders and talcum powders; hair care products such as shampoos, conditioners and hair dyes; and oral and dental care products such as toothpastes, mouthwashes, breath fresheners and coatings for dental flosses and tapes.

The whitened exine shell of the invention may be used as a delivery vehicle in a household product. Such a product may, for example, be selected from disinfectants and other antimicrobial agents, fragrances, perfume products, air fresheners, insect and other pest repellants, pesticides, laundry products (e.g. washing and conditioning agents), fabric treatment agents (including dyes), cleaning agents, UV protective agents, paints and varnishes.

The whitened exine shell of the invention may be used as a delivery vehicle for an active substance that is a pharmaceutical or dietetic (which includes nutraceutical) active substance, which includes substances for veterinary use. The active substance may be a pharmaceutically active substance which is suitable for topical delivery, for example selected from substances for use in treating skin or skin structure conditions (for example acne, psoriasis or eczema), wound or burn healing agents, anti-inflammatory agents, anti-irritants, antimicrobial agents (which can include antifungal and antibacterial agents), vitamins, vasodilators, topically effective antibiotics, antiseptics and agents providing skin protection against solar radiation. The active substance may be suitable and/or intended and/or adapted for oral delivery. It may therefore be suitable and/or intended and/or adapted for ingestion, by either humans or animals but in particular by humans. The active substance may be suitable and/or intended and/or adapted for pulmonary delivery, and/or for nasal delivery, and/or for intravenous delivery.

A pharmaceutically or nutraceutically active substance may be suitable and/or intended and/or adapted for either therapeutic or prophylactic use.

The whitened exine shell of the invention may be used as a delivery vehicle for an active substance that is a diagnostic agent, in particular one intended for oral ingestion. For instance, the active substance may be a radioactive tracer, or a magnetic tracer for use in magnetic resonance imaging. In such cases, a protective additive may help to ensure that the co-encapsulated active substance reaches its intended delivery site.

The whitened exine shell of the invention may be used as a delivery vehicle for incorporation of a substance into a food or beverage product, which terms include food and beverage ingredients. Food and beverage ingredients may include, for example, dietary supplements (such as vitamins and minerals, folic acid, omega-3 oils, fibre or so-called "probiotics" or "prebiotics"), flavourings, fragrances, essential oils, colourings, preservatives, stabilisers, emulsifiers and agents for altering the texture or consistency of a food product.

Particular examples include peptides (e.g. hormones such as insulin and growth hormones such as Somatropin); enzymes (e.g. lactase and alkaline phosphatase); probiotics (e.g. *Lactococcus lactis*, a Gram-positive bacterium); and prebiotics (e.g. carbohydrates such as lactulose, lactitol oligofructose, inulin and galacto-oligosaccharides, tagatose, isomalto-oligosaccharides, polydextrose and maltodextrin).

The whitened exine shell of the invention may be used as a delivery vehicle for an active substance which is a volatile substance, in particular a flavouring or fragrance.

An active substance may be chemically or physically bound to, or more particularly encapsulated within, a whitened exine shell according to the invention. Chemical and physical binding may be achieved for example in the ways described in WO-2005/000280, WO-2007/012856 and WO-2007/012857; they may involve chemical modification of the exine shell or at least of its outer surface.

A substance may be encapsulated within an exine shell using known techniques, again suitably as described in WO-2005/000280. Conveniently, prepared exine shells may be immersed in a solution or suspension of the relevant substance, which is then allowed to impregnate the shells, suitably followed by a drying step to remove at least some of the residual solvent(s). Where the substance to be encapsulated is a liquid, such as an oil, the prepared exine shells may simply be immersed in the liquid, which they will then absorb.

The exine shells are suitably immersed in an excess of the substance to be encapsulated within them. One or more penetration enhancing agents may be used, again as described in WO-2005/000280, to aid impregnation of the shell by the relevant substance. A reduced or increased pressure (with respect to atmospheric pressure) may instead or in addition be used to facilitate impregnation; for example, a mixture of exine shells and an active substance may be placed under vacuum in order to increase the rate of absorption of the active by the exine shells.

A substance may be generated in situ within an exine shell, for instance from a suitable precursor substance already associated with the shell. For example, a precursor substance may be chemically or physically bound to, or encapsulated within, an exine shell, which is then contacted with a reactant substance that reacts with the precursor to generate the desired active substance or additive.

The whitened exine shell may be loaded with, or otherwise associated with, any suitable quantity of an active substance, depending on its intended use. A formulation according to the invention may, for example, contain an active substance and whitened exine shells at a weight ratio of from 0.0001:1 to 15:1, such as from 0.0001:1 to 10:1, or from 1:1 to 10:1, or from 0.0001:1 to 5:1, or from 0.001:1 to 5:1 or 0.01:1 to 5:1 or from 0.1:1 to 5:1 or 0.5:1 to 5:1. Larger exine shells may be needed in order to achieve higher active substance loadings.

The exine shell may be coated with a barrier layer, for example for further protection of an associated active substance, to prevent its release until a desired time or location is reached, or for taste masking purposes. Such coatings may be as described in WO-2005/000280, WO-2007/012856 or WO-2007/012857.

Where the exine shell of the invention is used as an antioxidant, it can simply be contacted with a substance or composition to be protected. Instead or in addition, the substance or composition can be chemically or physically bound to, or encapsulated within, the shell. Suitable such methods are described in WO-2007/012856.

A formulation according to the second aspect of the invention may contain one or more additional agents for instance selected from fluid vehicles, excipients, diluents, carriers, stabilisers, surfactants, penetration enhancers or other agents for targeting delivery of the exine shell and/or an associated active substance to the intended site of administration.

The formulation may take the form of a lotion, cream, ointment, paste, gel, foam or any other physical form known for topical administration, including for instance a formulation which is, or may be, applied to a carrier such as a sponge, swab, brush, tissue, skin patch, dressing or dental fibre or tape to facilitate its topical administration. It may take the form of a viscous or semi-viscous fluid, or of a less viscous fluid such as might be used in sprays (for example nasal sprays), drops (e.g. eye or ear drops), aerosols or mouthwashes.

The formulation may alternatively take the form of a powder, for example when the active substance is a makeup product such as a blusher, eye shadow or foundation colour, or when it is intended for use in a dusting powder. Exine shells can be extremely efficient at absorbing liquids, in particular lipids, to result in an effectively dry product with all of the liquid encapsulated within the shells, as demonstrated in Example 11 of WO-2007/012856. Other active substances, for example food or beverage supplements or ingredients, or pharmaceutically or nutraceutically active substances, may also be formulated as powders.

For oral delivery, the formulation may for example take the form of a tablet, capsule, lozenge, solution or suspension, or of a food (including an animal feed) or beverage. Other suitable pharmaceutical and dietetic dosage forms are those disclosed in WO-2005/000280, for instance at pages 3 and 6 to 9.

If desired, the whitened exine shell may contain a protective additive which is co-encapsulated with an active substance, as described in PCT Application No. PCT/GB2008/004150. The active substance and the additive may be encapsulated within the exine shell either simultaneously or sequentially. In the former case, the active substance and additive may be mixed together, if necessary in an appropriate solvent system, and the mixture then encapsulated within the exine shell for instance using the immersion technique described above. In the latter case, the exine shell may be impregnated firstly with the active substance or a solution or suspension thereof and secondly with the protective additive or a solution or suspension thereof, if necessary with a drying step between the two impregnation steps.

It may be preferred for the active substance to be encapsulated before the additive, as this may serve to increase the protective effect of the additive. It is believed that, in such cases, the additive may form an at least partial protective layer around the outside of an active substance "core" and that, in some cases, the additive may at least partially coat the inside of the exine shell, thus blocking at least some of its pores.

In the foregoing, a "suspension" of an active substance or additive may be a dispersion, emulsion or any other multiphase system.

The additive may be a substance that is either solid or semi-solid under the normal storage conditions for the formulation (typically at room temperature). It may melt at a higher temperature (for instance, body temperature) at which the active substance is intended to be released from the formulation—examples of materials that behave in this way include cocoa butter and various fatty acids. The additive may be a material which is capable of masking, at least partially, the flavour and/or aroma of a co-encapsulated active substance.

Particularly suitable protective additives include (a) acrylic-based polymers such as the poly(alkyl)acrylates or poly(alkyl cyanoacrylates); (b) cellulosic materials, in particular cellulose-based polymers such as the cellulose acetate phthalates; (c) lipids; (d) materials having a lipid component, for example a lipid side chain, in particular fatty acids; and (e) polysaccharides.

In WO-2007/012856 it is disclosed that exine shells can themselves act as antioxidants and provide protection for example against UV-induced oxidation. This effect is believed to be additional to the physical barrier provided by the exine shell against the ingress of air. For many applications it is highly desirable to combine the ability to provide antioxidant protection with a high level of whiteness.

By analogy with the common general knowledge, it would be expected that oxidative bleaching would reduce or more likely remove the antioxidant effect. For example, the antioxidant effect of vitamin C is well known to be reduced following oxidation. Similarly, oxidative bleaching of carotenoids, which are well-known antioxidants, has been shown to destroy this property. Surprisingly, the present inventors have found that an exine shell which has been bleached according to the present invention generally retains a significant and useful level of antioxidant protection. The invention thus provides the use of such an exine shell as an antioxidant, and/or as a delivery vehicle for a substance which is sensitive to oxidation.

Throughout the description and claims of this specification, the words "comprise" and "contain" and variations of the words, for example "comprising" and "comprises", mean "including but not limited to", and do not exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Preferred features of each aspect of the invention may be as described in connection with any of the other aspects.

Other features of the present invention will become apparent from the following examples. Generally speaking the invention extends to any novel one, or any novel combination, of the features disclosed in this specification (including any accompanying claims and drawings). Thus, features, integers, characteristics, compounds, chemical moieties or groups described in conjunction with a particular aspect, embodiment or example of the invention are to be understood to be applicable to any other aspect, embodiment or example described herein unless incompatible therewith.

Moreover, unless stated otherwise, any feature disclosed herein may be replaced by an alternative feature serving the same or a similar purpose.

BRIEF DESCRIPTION OF THE FIGURES

The present invention will now be described by means of the following non-limiting examples, with reference to the following Figures in which.

EXAMPLES

Whiteness (L*) was measured using a Gretag Macbeath™ 7000 A Colour-eye instrument in reflectance mode and with the "D65" light source representing roughly a mid-day sun in western and northern Europe.

Samples were prepared by pressing 200 mg of exines in a standard infra-red press similar to the E-Z press (Available from Sigma-Aldrich, Product No. Z285889). A tablet 13 mm in diameter and 2 mm thickness was produced. Measurements were made by placing the tablet in the holder of the Colour-eye instrument. The area of view was 3 mm by 8 mm with a degree observer angle of 10°. The specular component was included. Measurements were generally made in duplicate and an average was taken.

Comparison 1

Comparison samples were prepared from *Lycopodium clavatum* (25 micron diameter). Raw *Lycopodium clavatum* spores (200.0 g) were suspended in acetone (750 ml) and heated under reflux for 4 hours. The spores were recovered by filtration (porosity grade 3) and then left to dry.

The spores were suspended in 6% KOH (w/v) (45.0 g, 750 ml) and heated under reflux for 6 hours. The spores were recovered by filtration (porosity grade 3) and washed with hot water (500 ml×2). The spores were re-suspended in fresh 6% KOH and heated under reflux for a further 6 hours. The spores were recovered by filtration (porosity grade 3) and washed with hot water (300 ml×3) and hot ethanol (300 ml×3) and left to dry. The spores were then refluxed in ethanol (750 ml) for 2 hours and filtered (porosity grade 3) and dried overnight in open air.

The spores were suspended in 85% ortho-phosphoric acid (w/v) (750 ml) and heated under reflux for 7 days. The spores were recovered by filtration (porosity grade 3) and washed with water (250 ml×5), acetone (300 ml×2), 2M HCl (300 ml×2), 2 M NaOH (300 ml×2), $H_2O$ (300 ml×2), ethanol (250 ml), acetone (250 ml) and then suspended in ethanol (900 ml) and stirred at 80° C. for 4 hours. The spores were recovered by filtration (porosity grade 3) and washed with ethanol (500 ml) and acetone (500 ml) and then dried under vacuum before further drying in an oven at 60° C. The resultant unbleached AHS exine shells were designated Comparison 1.

Comparison 2

Raw *Lycopodium clavatum* spores (200.0 g) were treated as in Comparison 1, except that following the base extraction and ethanol reflux, the spores were recovered by filtration (porosity grade 3), washed with ethanol (500 ml) and acetone (500 ml) and then dried under vacuum before further drying in an oven at 60° C. They were not subjected to any subsequent acid hydrolysis. The resultant unbleached BHS exine shell were designated Comparison 2.

Comparisons 3 and 4

The procedures of Comparisons 1 and 2 were repeated with spores of "*Lycopodium* Powder, Lab" (40 micron) commercially available from Post Apple Scientific.

The whiteness (L*) of Comparisons 1 to 4 were measured as described above. The results are presented in Table 1.

Example 1

Figure 1:
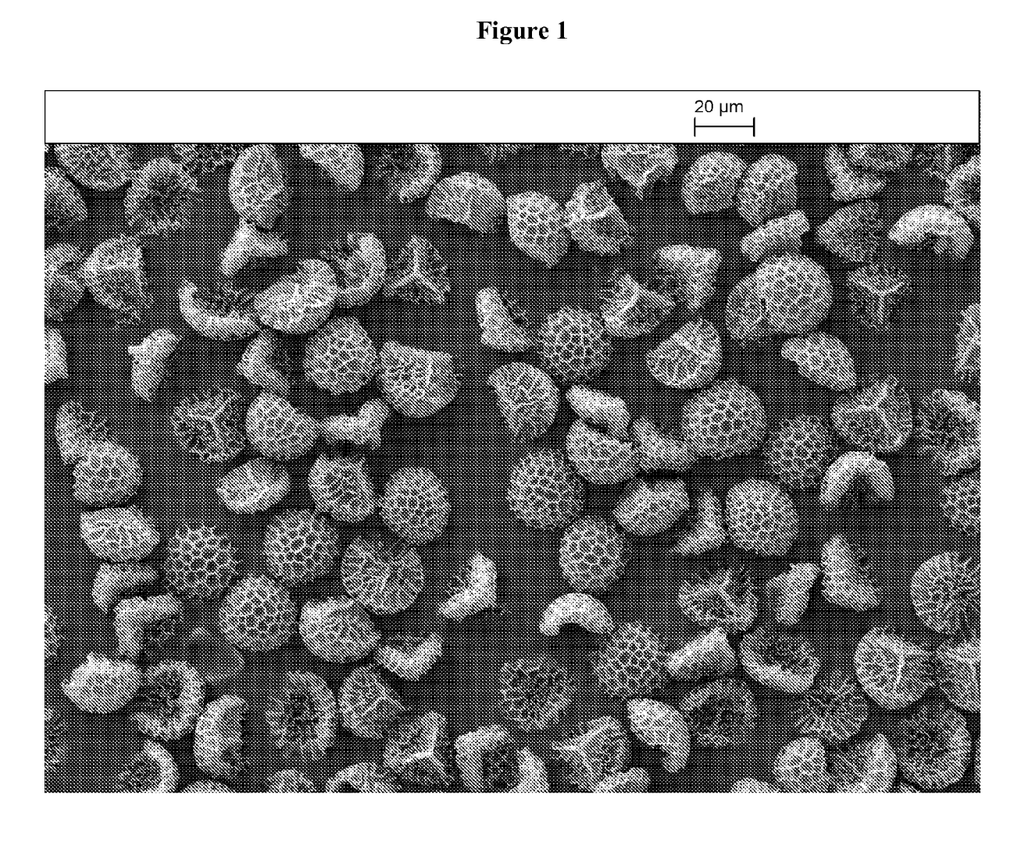
FIG. 1 is a scanning electron microscopy (SEM) image showing AHS shells after bleaching.

Fully hydrolysed AHS exine shells were prepared from *Lycopodium clavatum* (25 micron diameter) using the method of Comparison 1. The exine AHS shells (3.0 g) were suspended in glacial acetic acid (50 ml), saturated solution of sodium chlorate (9 ml) and conc. hydrochloric acid (3 ml). The mixture was stirred at 95° C. for 1 hour and then the exines recovered by filtration (porosity grade 3). The bleached exines were washed with water (50 ml×3), ethanol (50 ml×3) and diethyl ether (50 ml×2), and dried under vacuum over $P_2O_5$. The integrity of the structure of the resulting exines can be seen in FIG. 1. The product was formed into a tablet and its whiteness measured as described above.

Example 2

Figure 2:
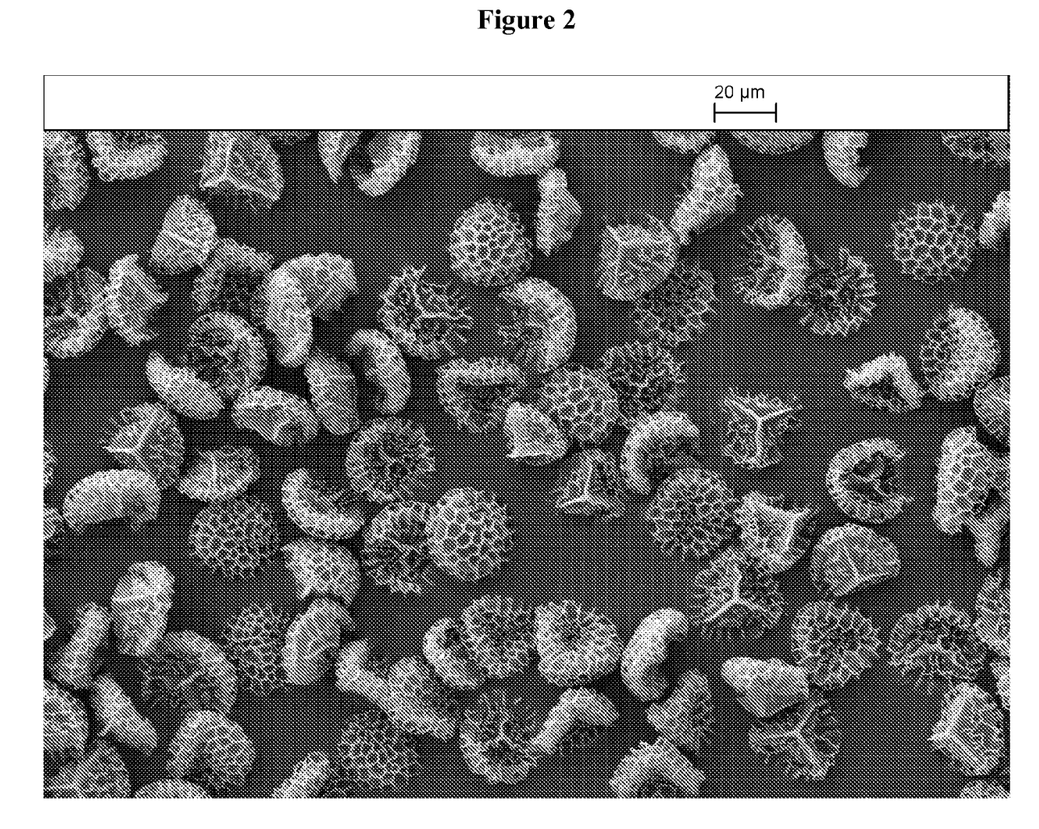
FIG. 2 is a SEM image showing BHS shells after bleaching.

Exine BHS shells prepared from *Lycopodium clavatum* (25 micron diameter) using the method of Comparison 2 were treated with a sodium chlorate bleaching agent as in Example 1. The integrity of the structure of the resulting exines can be seen in FIG. 2. The product was formed into a tablet and its whiteness measured as described above.

Example 3

Fully hydrolysed exine AHS shells were prepared from "*Lycopodium* Powder, Lab" (40 micron diameter) using the general method of Comparison 3. The exine shells were treated with a sodium chlorate bleaching agent as in Example 1. The product was formed into a tablet and its whiteness measured as described above.

Example 4

Exine BHS shells were prepared from "*Lycopodium* Powder, Lab" (40 micron diameter) using the general method of Comparison 4. The exine shells were treated with a sodium chlorate bleaching agent as in Example 1. The product was formed into a tablet and its whiteness measured as described above.

Example 5

Exine AHS shells were prepared from *Lycopodium clavatum* (25 micron diameter) using the method of Comparison 1. The exine AHS shells (3.0 g) were suspended in 7% sodium hypochlorite (w/v) solution and heated at 80° C. for 25 minutes. The exine shells were recovered by filtration (porosity grade 3) and washed with water (50 ml×3), ethanol (50 ml×3) and diethyl ether (50 ml×2), then dried under vacuum over $P_2O_5$. The product was formed into a tablet and its whiteness measured as described above.

Examples 6 and 7

The bleaching treatment of Example 5 was applied to BHS shells prepared from *Lycopodium clavatum* (25 micron) as described above and to BHS shells prepared from "*Lycopodium* Powder, Lab" (40 micron) as described above. In each case the product was formed into a tablet and its whiteness measured as described above.

Example 8

Exine AHS shells were prepared from *Lycopodium clavatum* (25 micron diameter) using the method of Comparison 1. The exine AHS shells (3.0 g) were suspended in 7% sodium hypochlorite solution and stirred at room temperature for 25 minutes. The exine shells were recovered by filtration (porosity grade 3) and washed with water (50 ml×3), ethanol (50 ml×3) and diethyl ether (50 ml×2), then dried under vacuum over $P_2O_5$. The product was formed into a tablet and its whiteness measured as described above.

Examples 9 to 11

The bleaching treatment of Example 9 was applied to BHS shells prepared from *Lycopodium clavatum* (25 micron) as described above and to AHS exine shells and BHS shells prepared from "*Lycopodium* Powder, Lab" (40 micron) as described above. In each case the product was formed into a tablet and its whiteness measured as described above.

Table 1 below shows the results for all of Examples 1 to 11 and Comparisons 1 to 4.

TABLE 1

Whiteness Measurements

| Example No | L* (D65) | Description |
| --- | --- | --- |
| Comparison 1 | 56.3 | 25 μm AHS |
| Comparison 2 | 61.1 | 25 μm BHS |
| Comparison 3 | 30.1 | 40 μm AHS |
| Comparison 4 | 51.2 | 40 μm BHS |
| Example 1 | 69.8 | 25 μm AHS Chlorate bleached 95° C. for 1 hour |
| Example 2 | 91.2 | 25 μm BHS Chlorate bleached 95° C. 1 hour |
| Example 3 | 66.1 | 40 μm AHS Chlorate bleached 95° C. 1 hour |
| Example 4 | 81.2 | 40 μm BHS Chlorate bleached 95° C. 1 hour |
| Example 5 | 74.4 | 25 μm AHS Hypochlorite bleached 80° C. 25 mins |
| Example 6 | 90.8 | 25 μm BHS Hypochlorite bleached 80° C. 25 mins |
| Example 7 | 83.2 | 40 μm BHS Hypochlorite bleached 80° C. 25 mins |
| Example 8 | 68.2 | 25 μm AHS Hypochlorite bleached 25 mins |

TABLE 1-continued

Whiteness Measurements

| Example No | L* (D65) | Description |
|---|---|---|
| Example 9 | 86.3 | 25 μm BHS Hypochlorite bleached 25 mins |
| Example 10 | 75.7 | 40 μm BHS Hypochlorite bleached 25 mins |
| Example 11 | 91.3 | 25 μm AHS Hypochlorite bleached 60° C. 2 hours |

Example 12

Raw *Lycopodium clavatum* spores (200.0 g) were suspended in acetone (900 ml) and stirred at 60° C. for 4 hours. The spores were recovered by filtration (porosity grade 3) and washed with acetone (250 ml) and then left to dry. They were then suspended in 6% KOH (w/v) (54.0 g, 900 ml) and stirred at 80° C. for 6 hours. The spores were recovered by filtration (porosity grade 3) and washed with hot water (500 ml×2). The spores were re-suspended in fresh 6% KOH and heated at 80° C. for a further 6 hours. The spores were recovered by filtration (porosity grade 3) and washed with hot water (500 ml×6) and left to dry.

The spores were suspended in 85% ortho-phosphoric acid (w/v) (800 ml) and stirred at 60° C. for 5 days. The spores were recovered by filtration (porosity grade 3) and washed with hot water (500 ml×2), 2 M NaOH (500 ml×2), hot water (500 ml×6), PBS (250 ml×2) and hot water (500 ml×2), and then suspended in EtOH (900 ml) and stirred at 80° C. for 4 hours. The spores were recovered by filtration (porosity grade 3) and washed with ethanol (500 ml) and acetone (500 ml), then dried under vacuum before further drying in an oven at 60° C.

The resultant exine AHS shells (1.04 g) were suspended in 50 ml of a 7% sodium hypochlorite solution and stirred at 60° C. for 2 hours. The spores were recovered by filtration (porosity grade 3) and washed with water (50 ml×3), ethanol (50 ml×3) and acetone (50 ml×3), then dried overnight in open air and further dried under vacuum over $P_2O_5$. The product was formed into a tablet and its whiteness measured as described above. The results are presented in Table 2. The whiteness of the product before bleaching is included as a comparison.

Example 13

The bleaching treatment of Example 12 was applied to BHS shells prepared from *Lycopodium clavatum* (25 micron) as follows: Raw *Lycopodium clavatum* spores (199.3 g) were suspended in acetone (900 ml) and stirred at 60° C. for 4 hours. The spores were recovered by filtration (porosity grade 3) and washed with acetone (250 ml) and then left to dry. The spores were suspended in 6% KOH (w/v) (54.0 g, 900 ml) and stirred at 80° C. for 6 hours. The spores were recovered by filtration (porosity grade 3) and washed with hot water (500 ml×2). The spores were re-suspended in fresh 6% KOH and heated at 80° C. for a further 6 hours. The spores were recovered by filtration (porosity grade 3) and washed with hot water (500 ml×8), PBS (250 ml×2) and hot water (500 ml×2) and then suspended in EtOH (900 ml) and stirred at 80° C. for 4 hours. The spores were recovered by filtration (porosity grade 3) and washed ethanol (500 ml) and acetone (500 ml) and then dried under vacuum before further drying in an oven at 60° C.

The bleaching step using 7% sodium hypochlorite solution, as described above in Example 12, was then applied.

The product was formed into a tablet and its whiteness measured as described above. The results are presented in Table 2. The whiteness of the products before bleaching are included as comparisons.

TABLE 2

Whiteness Measurements

| Example No | L* (D65) | Description |
|---|---|---|
| 12 (Comparison) | 63.2 | Unbleached 25 μm AHS |
| 12 | 92.6 | Bleached 25 μm AHS |
| 13 (Comparison) | 54.2 | Unbleached 25 μm BHS |
| 13 | 90.3 | Bleached 25 μm BHS |

Comparative Example 14

Using the general method of *Svensk Botanisk Tidskrift*, 54, 4 1960 (G Erdtman), ryegrass spores (10.0 g) were suspended in an acetolysis mixture consisting of acetic anhydride (190 ml) and concentrated sulfuric acid (10 ml) and stirred at 60° C. overnight. The spores were recovered by filtration (porosity grade 3) and washed with acetic anhydride (200 ml×5), ethanol (200 ml×5) and diethyl ether (200 ml×5), then dried under vacuum over $P_2O_5$. The resultant exine shells had a whiteness of 43.1.

The extracted exine shells (5.0 g) were suspended in glacial acetic acid (50 ml), a saturated solution of sodium chlorate (5 ml) and conc. hydrochloric acid (5 ml). The mixture was stirred at room temperature for 10 minutes and then the exines recovered by filtration (porosity grade 3). The bleached exines were washed with water (100 ml×3), ethanol (100 ml×2) and diethyl ether (100 ml×2), then dried under vacuum over $P_2O_5$. The product had a whiteness of 58.9.

Example 15

The ability of whitened exine shells according to the invention to act as antioxidants was determined by making a series of measurements over time of the peroxide value of cod liver oil containing the shells. The peroxide value (PV) is an indication of the degree of oxidation that has taken place. The products of Examples 1, 2, 5, 6, 8 and 9 were evaluated and compared with a control sample of cod liver oil containing no exine shells.

Figure 3:
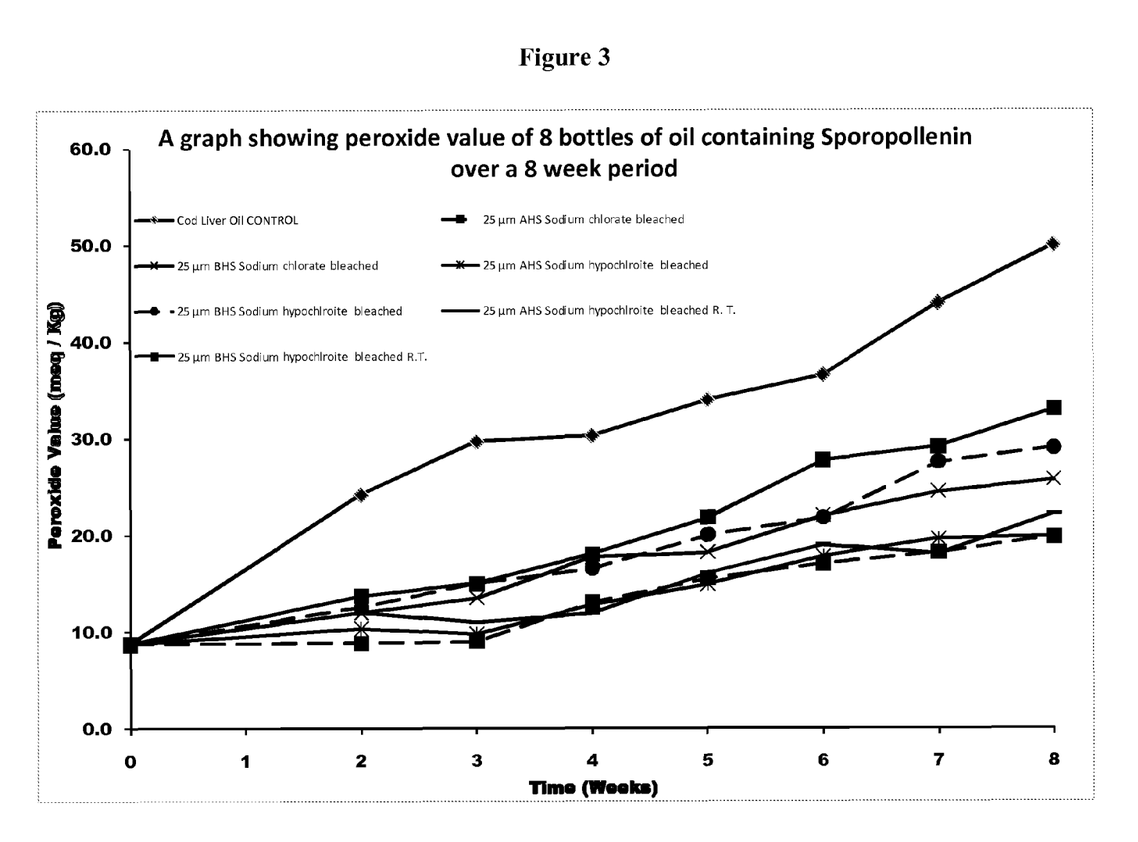
FIG. 3 is a graph showing the change in peroxide value over time of the formulations tested in Example 15 below.

500 mg of each of the indicated samples of bleached sporopollenin exine shells were placed in 50 ml glass bottles, with plastic stoppers. The bottles were filled with 50 ml of fresh cod liver oil. The samples were shaken and left to settle. Then every week, on the same day, the peroxide value was measured for each bottle according to IUPAC standard method 2.500. The results are shown in Table 3 and FIG. 3, which is a plot of the same data. It can be seen that all the bleached exine shells of the invention retain excellent antioxidant properties over a period of at least eight weeks.

TABLE 3

Peroxide Values of Samples

| Time (weeks) | Control | Ex. 1 | Ex. 2 | Ex. 5 | Ex. 6 | Ex. 8 | Ex. 9 |
|---|---|---|---|---|---|---|---|
| 0 | | | | 8.7 | | | |
| 2 | 24.2 | 8.8 | 12.0 | 10.3 | 12.5 | 12.0 | 13.7 |
| 3 | 29.7 | 9.0 | 13.5 | 9.8 | 15.0 | 11.0 | 15.0 |
| 4 | 30.3 | 13.0 | 17.7 | 12.8 | 16.5 | 11.9 | 18.0 |
| 5 | 34.0 | 15.5 | 18.2 | 14.9 | 20.0 | 16.0 | 21.8 |
| 6 | 36.6 | 17.0 | 22.0 | 17.8 | 21.8 | 19.0 | 27.7 |
| 7 | 44.0 | 18.2 | 24.5 | 19.6 | 27.5 | 18.0 | 29.1 |
| 8 | 50.0 | 19.8 | 25.7 | 19.8 | 29.0 | 22.2 | 33.0 |

Example 16

Exine shells of *Secale cereale* (cereal rye) were extracted and then bleached using the following procedure. *Secale cereale* pollen (6.01 g) was subjected to enzyme-catalysed hydrolysis by suspension in water (50 ml) containing cellulase enzyme (derived from *Aspergillus niger*, Sigma) (60 mg) and stirring at 40° C. for 1 hour. The pollen was recovered by centrifugation (3000 rpm, 10 mins) and washed by filtration (porosity grade 3) with water (50 ml×3), ethanol (50 ml×2), acetone (50 ml) and left to dry in air. The extracted exines (2.095 g) were suspended in 0.1% hydrogen peroxide (20 ml), stirred and filtered (porosity grade 3) immediately. The spores were washed with water (20 ml×3), ethanol (20 ml×2), acetone (20 ml) and left to dry in air.

The whiteness (L*) of the shells, measured as described above, was 73.9 prior to bleaching and 75.4 afterwards.

The antioxidant activity of the bleached shells was tested using the procedure described in Example 15. The results showed an overall protection from the exine shells of 17% based on periodic PV determinations over the 10 weeks. The unprotected cod liver oil reached a PV value of 20 after 4.6 weeks, whereas the oil protected by the exine shells did not reach this value until 5.7 weeks. After 10 weeks the average PV values were 34 for the unprotected oil and 28 for the exine-protected sample.

The invention claimed is:

1. A whitened exine shell having a degree of whiteness (L*) of greater than 65 measured under D 65 illumination.

2. A whitened exine shell according to claim 1, which has a degree of whiteness (L*) of greater than 75 measured under D 65 illumination.

3. A formulation containing a whitened exine shell according to claim 1, together with an active substance.

4. A formulation according to claim 3, which is a food product, a beverage product, a cosmetic product, or a pharmaceutical or dietetic (which includes nutraceutical) product.

5. A method for preparing a whitened exine shell, the method involving isolating an exine shell from a naturally occurring spore under treatment conditions which do not include acetolysis, and treating the isolated exine shell or a precursor thereof with a bleaching composition.

6. A method according to claim 5 involving isolating an exine shell from a naturally occurring spore under hydrolysis treatment conditions, and treating the isolated exine shell or a precursor thereof with a bleaching composition.

7. A method according to claim 5, wherein the bleaching composition is applied to the isolated exine shell.

8. A method according to claim 5, the exine shell product of which has a degree of whiteness (L*) of greater than 65 measured under D 65 illumination.

9. A method of surgery, therapy or diagnosis practised on a living human or animal body comprising use of a whitened exine shell according to claim 1.

10. A method for protecting an active substance from oxidation and/or for increasing the stability of the active substance or of a composition containing it, the method comprising formulating the active substance with a whitened exine shell according to claim 1.

11. A method of improving the whiteness of an exine shell which has been isolated from a naturally occurring spore under conditions which do not include acetolysis, the method involving treating the isolated exine shell or a precursor thereof with a bleaching composition.

12. A method according to claim 11 wherein the exine shell has been isolated from a naturally occurring spore under hydrolysis conditions.

13. A method according to claim 9 wherein the whitened exine shell is a delivery vehicle for an active substance.

14. A formulation according to claim 3, which is a food product.

15. A formulation according to claim 3, which is a beverage product.

16. A formulation according to claim 3, which is a cosmetic product.

17. A formulation according to claim 3, which is a pharmaceutical or dietetic (which includes nutraceutical) product.

* * * * *

UNITED STATES PATENT AND TRADEMARK OFFICE
CERTIFICATE OF CORRECTION

PATENT NO. : 8,828,464 B2  
APPLICATION NO. : 13/001767  
DATED : September 9, 2014  
INVENTOR(S) : Stephen Atkin et al.

Page 1 of 1

It is certified that error appears in the above-identified patent and that said Letters Patent is hereby corrected as shown below:

In the Claims:

1. In line 2 of claim 1 (column 19, line 43) after 'illumination', insert --, wherein the exine shell is continuous over at least 75% of the surface area which an exine shell from the relevant species would have if intact--.

2. In line 1 of claim 5 (column 20, line 6) after 'shell', insert --according to claim 1--.

3. In line 2 of claim 5 (column 20, line 7) after 'method', delete "involving" and insert --comprising-- therefor.

4. In line 1 of claim 6 (column 20, line 11) after 'claim 5', delete "involving" and insert --comprising-- therefor.

5. In line 4 of claim 11 (column 20, line 31) after 'method', delete "involving" and insert --comprising-- therefor.

6. In line 5 of claim 11 (column 20, line 32) after 'composition', insert --, to produce a whitened exine shell according to claim 1--.

Signed and Sealed this  
Thirteenth Day of January, 2015

Michelle K. Lee  
*Deputy Director of the United States Patent and Trademark Office*